US006335959B1

(12) United States Patent
Lynch et al.

(10) Patent No.: US 6,335,959 B1
(45) Date of Patent: Jan. 1, 2002

(54) APPARATUS AND METHOD FOR DETERMINING OIL WELL EFFLUENT CHARACTERISTICS FOR INHOMOGENEOUS FLOW CONDITIONS

(75) Inventors: Frank Joseph Lynch; Gary John Miller, both of Glasgow (GB)

(73) Assignee: Daniel Industries, Inc.

( * ) Notice: Subject to any disclaimer, the term of this patent is extended or adjusted under 35 U.S.C. 154(b) by 0 days.

(21) Appl. No.: 09/679,081

(22) Filed: Oct. 4, 2000

Related U.S. Application Data

(60) Provisional application No. 60/157,441, filed on Oct. 4, 1999.

(51) Int. Cl.[7] .............................................. G01N 23/223
(52) U.S. Cl. ..................... 378/45; 250/356.1; 73/61.44; 378/47; 378/50
(58) Field of Search ........................... 73/61.44, 861.04; 208/108; 250/356.1

(56) References Cited

U.S. PATENT DOCUMENTS

| | | | |
|---|---|---|---|
| 4,144,754 A | 3/1979 | Pitts, Jr. et al. ................ | 73/205 |
| 4,282,760 A | 8/1981 | Pitts, Jr. et al. ........... | 73/861.02 |
| 4,582,680 A | 4/1986 | Bar-Cohen et al. ............ | 419/23 |
| 5,025,160 A | * 6/1991 | Watt ......................... | 250/356.1 |
| 5,047,632 A | * 9/1991 | Hunt .......................... | 250/302 |
| 5,259,239 A | * 11/1993 | Gaisford ..................... | 73/61.44 |
| 5,591,922 A | 1/1997 | Segeral et al. ............ | 73/861.04 |
| 5,654,551 A | 8/1997 | Watt et al. ................. | 250/356.1 |
| 5,854,820 A | 12/1998 | Slijkerman et al. ............ | 378/51 |
| 6,028,992 A | 2/2000 | Henriot et al. ............. | 395/500.3 |
| 6,076,049 A | 6/2000 | Lievois et al. .............. | 702/100 |

FOREIGN PATENT DOCUMENTS

| | | | |
|---|---|---|---|
| EP | 0 001 320 | 7/1978 | ........... F15B/13/14 |
| EP | 0696354 | 11/1994 | |

* cited by examiner

Primary Examiner—Robert H. Kim
Assistant Examiner—Pamela R. Hobden
(74) Attorney, Agent, or Firm—Conley, Rose & Tayon, P.C.

(57) ABSTRACT

An apparatus and method for determining the phase volume fractions for a multiphase oil well effluent is disclosed. The apparatus measures multiple energy gamma ray attenuations through the effluent mixture, and the method determines the phase volume fractions from these measurements when the mixture is under inhomogeneous flow conditions. The apparatus includes a pipe section with a Venturi through which the mixture flows. A source of radiation transmits rays at two or more energy levels through the mixture. A solid state detector measures the transmitted attenuation count rates. A low absorption window of a truncated cone shape is preferably incorporated in lieu of the pipe wall in the area of the detector. The method comprises measuring ray attenuation, in the two-energy example, at one high energy emission line, to differentiate between the gas and liquid components, and at a relatively lower energy emission line, to differentiate between the oil and water phases within the liquid component. The attenuation count rates for one energy level are measured over short time intervals relative to the measurement period for the attenuation count rates at the second energy level. Through a series of calculations, the actual measured total count rates for each energy level are corrected to equivalent homogeneous count rates. The corrected count rates can then be used in homogeneous flow equations to determine the phase volume fractions. In this manner, the water, oil and gas volume fractions of the mixture are determined.

24 Claims, 6 Drawing Sheets

APPARATUS AND METHOD FOR DETERMINING OIL WELL EFFLUENT CHARACTERISTICS FOR INHOMOGENEOUS FLOW CONDITIONS

CROSS-REFERENCE TO RELATED APPLICATIONS

The present application claims the benefit of 35 U.S.C. 111(b) provisional application Ser. No. 60/157,441 filed Oct. 4, 1999, and entitled "Apparatus and Method for Determining Oil Well Effluent Characteristics For Inhomogeneous Flow Conditions."

STATEMENT REGARDING FEDERALLY SPONSORED RESEARCH OR DEVELOPMENT

Not applicable.

BACKGROUND OF THE INVENTION

1. Field of the Invention

The present invention generally relates to an apparatus and method for characterizing multiphase oil well effluents, typically comprising water, crude oil and gas, using measurements associated with the fluid mixture. More particularly, the present invention relates to an apparatus for measuring multiple energy gamma ray attenuations through the effluent mixture and a method for determining the effluent phase volume fractions of water, oil and gas from these measurements. Still more particularly, a preferred embodiment of the present invention relates to an apparatus and method for determining effluent phase volume fractions for an inhomogeneous flow condition using the gamma ray attenuation measurements.

2. Background of the Invention

Advances in petroleum drilling and production technology make it possible to economically explore and produce oil and gas in areas that were previously inaccessible, such as deepwater offshore fields. New technologies also provide opportunities to maximize oil and gas recoveries from existing offshore and onshore reservoirs. Producing these fields economically requires optimized production methods, improved production allocations, enhanced reservoir management, and accurate pipeline measurement. To accomplish these objectives, producers and pipeline operators must determine, as accurately as possible, oil well effluent characteristics.

Oil well effluents are multiphase fluids typically comprising water, oil and gas phases. Total mixture flow rate, component phase flow rates, and effluent composition (i.e. the phase volume fractions of water, oil and gas) are all important to producers and pipeline operators. By evaluating these characteristics, a producer can take corrective action when necessary to optimize production operations over the life of the field and thereby enhance reservoir management. Once an oil well effluent is produced, it is typically transported through pipelines to treating facilities. Knowledge of oil well characteristics is also critical in pipeline measurement applications for leak detection and custody transfer measurement purposes.

In practice, developing a method for accurately determining oil well effluent characteristics has been challenging due to the multiphase nature of the fluid and its varying flow conditions. As effluent is produced or transported, it is exposed to changing pressures, temperatures and pipe configurations that create inhomogeneous, unstable, and unpredictable flow patterns in the multiphase fluid. An especially problematic flow condition is the slug flow regime where phase stratification occurs causing the gas to come out of solution and form pockets apart from the liquid phase. As the effluent moves in the slug flow regime, gas and liquid sections alternate at varying frequencies, thereby affecting the accuracy of standard liquid flow meters designed to perform in single-phase liquids. The industry refers to the gas and liquid sections as either gas "slugs" and liquid "plugs" or gas "films" and liquid "slugs." The former "slug and plug" industry nomenclature will be used herein.

The traditional oil industry practice for determining effluent characteristics has been to periodically divert the well output to a test separator to split the effluent into its component phases. Once the phases are separated, they are then measured independently using conventional orifice, positive displacement, or turbine meter devices as appropriate for the phase being measured. This operation has several inherent limitations. Separators are physically large, costly, and particularly ill-suited for use offshore where platform space is scarce and enlarging the platform can significantly increase capital costs. From a measurement standpoint, it is often impractical for each well to have a dedicated separator so several wells typically share a common separator making continuous well effluent monitoring impossible. Additionally, stabilized well flow is necessary for accurate measurement, and testing the effluent from just one well can take up to a whole day.

Over the past twenty years, various devices and techniques have been proposed for on-line multiphase fluid measurements that eliminate the need for separators. Most suggest a combination of measurement sensors for separately determining total flow rate and volume fractions of one or more of the phases.

U.S. Pat. No. 4,144,754, incorporated by reference herein for all purposes, describes one of the first multiphase meters. The apparatus comprises a flow loop and a gamma ray densitometer. The flow loop exerts centrifugal force on the fluid mixture that generates differential pressure on the fluid between the inner and outer walls of the loop. The densitometer measures the fluid mixture density. By correlating the differential pressure and density the total mixture flow rate can be determined. Wile this meter is applicable for fluids of unknown or varying density, it does not seem to accurately account for the "slip" phenomenon that occurs when the gas phase flow rate differs from the mixture flow rate. To resolve this problem, mixing devices may be added upstream of the flow meter to homogenize the flow and equalize flow velocities; however this solution adds to the capital costs and increases the required space for the measurement equipment.

U.S. Pat. No. 4,282,760, incorporated herein for all purposes, describes a method for improved measurement accuracy that accounts for the slip phenomenon and determines liquid (oil and water) and gas mass flow rates. The method makes use of multiple densitometers to measure mixture, liquid and gas densities and correlate those measurements with differential pressure to determine total, liquid and gas phase mass flow rates. Although improving measurement accuracy, more equipment is required, thereby adding to the complexity and cost.

Since the early days of multiphase measurement, numerous methods for accomplishing accurate measurement have been proposed, including capacitance techniques, reflection or scatter techniques, and transmission techniques based on measurements of neutrons, infrared, ultrasonics, microwaves, or gamma rays. U.S. Pat. No. 5,591,922, incorporated herein for all purposes, describes a method and apparatus for determining multiphase effluent phase proportions and mass flow rates for the mixture and for each component phase. The apparatus comprises a Venturi and a device for measuring gamma ray or X-ray attenuation at three different energy levels correlating with and proportional to each effluent phase to be measured. A low absorption window may be incorporated into the Venturi section of the pipeline to increase the transmission of radiation through the crude oil, and a gas-charged, proportional counter tube detector is used to measure gamma ray attenuation.

Several advances and improvements have been made over the basic Venturi and gamma ray source/detector apparatus and method. PCT Application EP94/01320, the contents of which are incorporated by reference for all purposes, discloses an improvement to the apparatus gamma ray window by employing a lining of carbon fiber reinforced resin (CFRE) within the meter conduit. The lining forms a window with the advantages of low radiation absorption while allowing relatively high internal pressures to be applied.

European Patent Specification EP 0,696,354 B1, the contents of which are incorporated by reference for all purposes, discloses an improvement to the gamma ray detector design by employing a dual area solid-state semiconductor diode detector for improved measurement accuracy in detecting both low and high-energy emission lines. Since detector efficiency is significantly lower at high-energy emission lines, the efficiency of the detector is improved by providing a solid state detector configuration with at least two radiation detecting surfaces. A filter is located between the radiation source and the first detecting surface to prevent the low energy radiation from passing through to that detecting surface. In this manner, one detecting surface is specifically employed to measure high-energy emission lines and the other detecting surface measures low energy emission lines. The resolution and efficiency of this detector configuration is further improved by providing a suitable cooling means forming a Peltier element to maintain the detector temperature at 0–15 degrees Celsius. EP 0,696,354 B1 and PCT Application EP94/01320 each disclose a method of acquiring measurements at five low energy gamma ray energy emission lines using Americium-241 to improve measurement accuracy. Having more than two energy emission lines can improve measurement accuracy by comparing effluent composition determinations at various energy levels and applying a least squares fit. Additionally, U.S. Pat. No. 5,854,820, incorporated by reference herein for all purposes, discloses a method for determining produced water salinity by using a third energy emission line in addition to the minimum two energy emission lines required to determine phase volume fractions. Compensation for variations in produced water salinity can improve the accuracy of phase volume fraction calculations and reduce meter calibration requirements.

Gamma ray, X-ray and other transmission techniques are generally considered superior to reflection or scatter techniques for determining fluid volumes across the pipe. Transmission techniques are therefore preferred for accurate flow rate determinations in homogeneous fluid mixtures of oil, water and gas. One shortcoming, however, is the requirement of a long radiation path length in liquid to obtain adequate sensitivity for determining volume and mass fractions. These transmission techniques can therefore be inadequate for inhomogeneous flow regimes such as stratified flow or slug flow where liquid plugs and gas slugs alternate frequently and measurements taken during a gas slug will introduce measurement inaccuracies.

To overcome this difficulty, several approaches have been suggested for determining effluent characteristics under inhomogeneous flow conditions. U.S. Pat. No. 5,654,551, incorporated by reference herein for all purposes, discloses a method for measuring phase mass flow rates using several gamma ray source/detector devices. Gamma ray attenuation measurements are taken in the traditional way while one source/detector device is used solely to detect the beginning and ending of each gas slug or liquid plug. This method of compensation seems to be directed only at correcting for inhomogeneous flow in the slug flow regime and would appear to be inadequate for measurements in another type of inhomogeneous flow such as stratified flow.

Similarly, PCT Application EP98/05239, the contents of which are incorporated by reference for all purposes, discloses a method for measurement compensation particularly directed at the slug flow regime where measurements are acquired at high frequencies compared to the gas/liquid alternation cycle and these measurements are averaged over a time corresponding to a low frequency compared to the gas/liquid alternation cycle. The averaged values are used in calculations to determine effluent characteristics. This method uses a confidence coefficient, determined as a function of density, that is applied to weight the water to liquid ratio calculated for each high frequency sample.

Even with these substantial advances in multiphase metering, however, substantial problems still exist. For example, the accuracy of multiphase measurement for determining phase volume fractions remains undesirably low for inhomogeneous flow regimes. In light of the significant volumes of effluent produced, these errors can seriously and negatively impact production operations, lead to inefficient reservoir management and generate substantial financial miscalculations between a buyer and seller of the hydrocarbon stream. Thus, it would be desirable to develop an apparatus or method to provide accurate, timely measurement data for key parameters of the effluent stream resulting in efficient well management and production optimization.

Ideally, this method or apparatus would overcome limitations of earlier compensation methods for improving the accuracy of phase fraction determinations for all types of inhomogeneous flow, not just for the slug flow regime. The preferred embodiment of the present invention provides a solution to this limitation by applying a correction factor to convert an inhomogeneous gamma ray count rate to an effective homogeneous gamma ray count rate, thereby making the homogeneous flow equations applicable for determining phase volume fractions.

SUMMARY OF THE INVENTION

The present invention relates to an apparatus and method for determining the phase volume fractions for a multiphase oil well effluent, typically comprising water, crude oil and gas. More particularly, the present invention relates to an apparatus for measuring multiple energy gamma ray attenuations through the effluent mixture and a method for determining the effluent phase volume fractions of water, oil and gas from these measurements when the mixture is under inhomogeneous flow conditions.

The apparatus comprises a pipe section including a converging Venturi. The Venturi induces a pressure drop as the mixture flows through the pipe section. The preferred embodiment includes a removable central Venturi nose cone, which allows the meter flow rate range to be modified in situ by exchanging the central Venturi nose cone.

A radiation source produces radioactive rays (i.e. gamma or X-rays) at two or more energy levels that pass through the mixture perpendicular to the flow stream. These radioactive rays are attenuated to varying degrees, depending upon their energies and on the fractions of water, oil and gas present. One exemplary embodiment of the present invention utilizes an Americium-241 radioactive gamma ray source.

A solid state detector measures the transmitted gamma ray count rates at each energy level. In the exemplary embodiment, the solid state detector comprises two or more radiation detecting surfaces and a filter preventing certain of the energy levels from passing through to the detecting surface. The preferred detector also includes a suitable cooling means, such a Peltier element, which enhances the resolution and allows the detector to distinguish between the closely spaced low-energy lines from the radioactive source.

A section or window formed of a low radiation absorption material such as, for example, Carbon Fiber Reinforced Epoxy (CFRE) or boron carbide, is preferably incorporated in the area of the detector in lieu of the pipe wall to increase the transmission of radiation to the detector. The preferred window configuration is a specially designed truncated cone shape that optimizes the window strength, allowing it to withstand high internal pressures, while also lowering absorption of radiation through the window as compared to prior art configurations.

The method comprises measuring the gamma-ray attenuation, in the two-energy example, at one high-energy emission line (E1), to help differentiate between the liquid and gas components, and at one low-energy emission line (E2), to help differentiate between the water and oil phases. To correct for the distorting effects of inhomogeneous flow, the attenuation count-rates at E1 are measured over short time intervals compared to the measurement period for E2.

The attenuation count rates for E1 are used to estimate the gas/liquid distribution over the measurement period by calculating a liquid fraction. An important parameter required in determining the gas/liquid distribution is the water-cut, w, of the liquid phase. As this is not known a priori, a best estimate is entered into the liquid fraction calculation.

Using the calculated liquid fraction, theoretical inhomogeneous and homogeneous count rates for each energy level are calculated. Correction factors, based on the theoretical homogeneous/inhomogeneous count-rate ratios, are then applied to the total measured count rates at each energy level to yield corrected (i.e. equivalent homogeneous) total count-rates. These corrected total count-rates may then be entered into homogeneous flow equations to yield estimates of the phase volume fractions and a better estimate for the water-cut. The entire calculation is iterated until no further improvement is gained in the derived phase fractions.

BRIEF DESCRIPTION OF THE DRAWINGS

For a detailed description of the preferred embodiments of the invention, reference will now be made to the accompanying drawings in which.

NOTATION AND NOMENCLATURE

During the course of the foregoing and following description, the term "homogeneous" is used to describe a multiphase flow stream where the effluent phase percentages are uniform so that the same proportions of water, oil, and gas are present at any point along the pipe section. The term "inhomogeneous" flow is use to describe a multiphase flow stream where the effluent phase percentages vary so that differing proportions of water, oil and gas are present at any point along the pipe section.

DETAILED DESCRIPTION OF THE PREFERRED EMBODIMENTS

Figure 1:
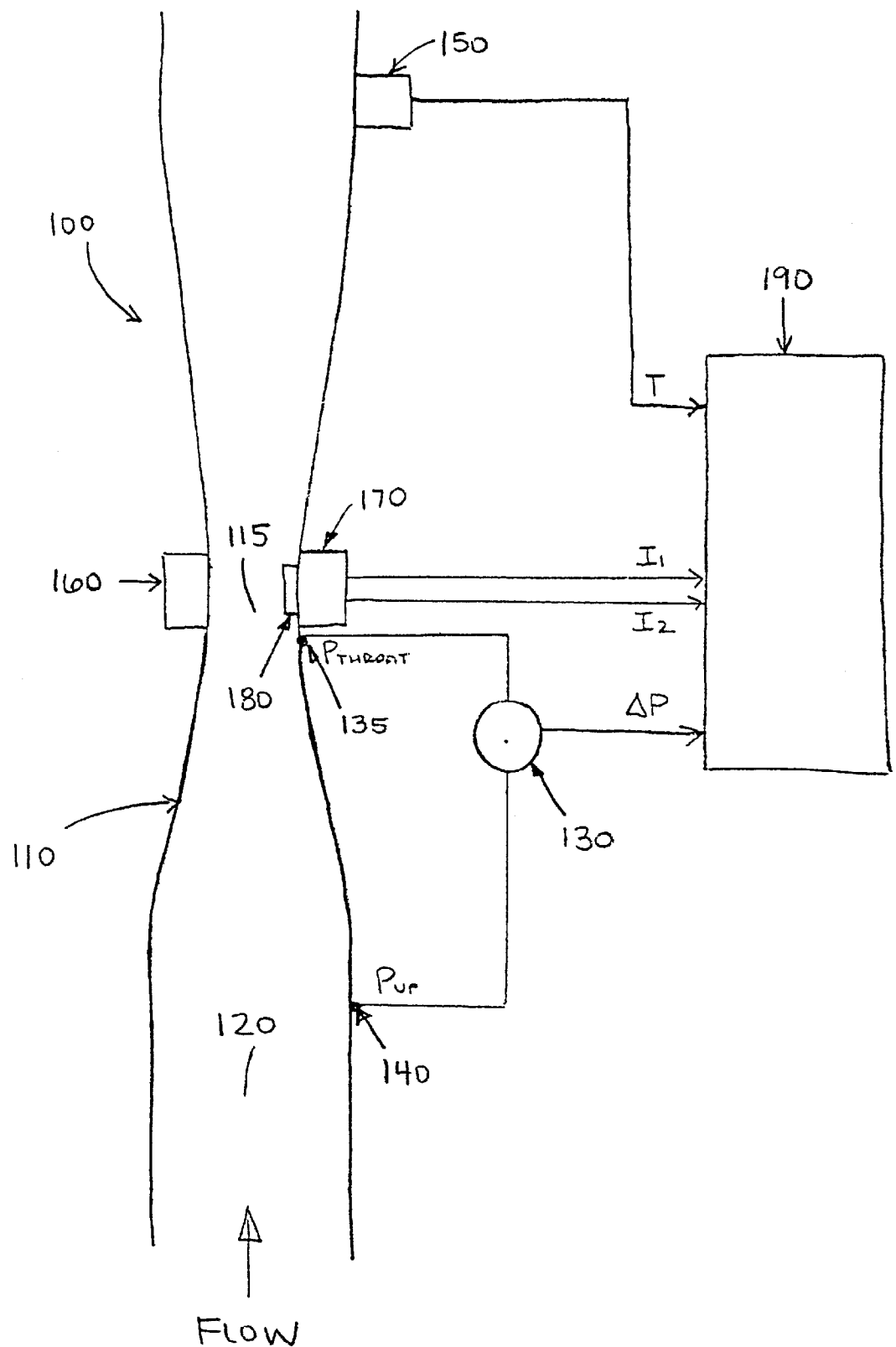
FIG. 1 shows a diagrammatic view of a pipe section incorporating a measurement apparatus for characterizing an oil well effluent, in accordance with one embodiment, including a Venturi section and a device for measuring gamma ray attenuation.

FIG. 1 shows a measurement apparatus used to determine characteristics of a multiphase effluent comprising water, crude oil and gas phases, either as a homogeneous or inhomogeneous mixture. The apparatus comprises a pipe section 100 provided with a converging Venturi 110 whose narrowest portion 115 is referred to as the "throat." The pipe section 100 is shown disposed vertically with flow up through the Venturi 110 as symbolized by the flow arrow. As the effluent flows through the Venturi 110, the throat 115 induces a pressure drop $\Delta p$ between upstream level 120 and throat 115. The pressure drop is measured by means of a differential pressure transmitter 130 connected to transducers at pressure measurement ports 135 and 140. Port 140 corresponds to upstream level 120 and port 135 corresponds to throat 115. Temperature transmitter 150 can be located anywhere along the measurement section.

At the same time, a radiation source 160 produces radioactive rays (i.e. gamma or X-rays) at two or more energy levels. As the radioactive rays pass through the fluid, they are attenuated to varying degrees, depending upon their energies and on the fractions of water, oil and gas present. Detector 170 measures the transmitted gamma ray count rates representing the number of photons detected per measurement period at each energy level. For example, gamma ray count rates I1 and I2 would be measured if two energy levels are being used. A low absorption window 180 may be incorporated in the throat 115 in lieu of the pipe wall to increase the transmission of radiation to the detector.

The preferred embodiment describes a method for improving the accuracy of phase volume fraction determinations for inhomogeneous flow regimes. These higher accuracy phase volume fractions can then be incorporated into other calculations to improve the accuracy of density and flow rate determinations. Signals from differential pressure transmitter 130, temperature transmitter 150, and gamma ray detector 170 are fed to processor 190 where calculations are performed to determine effluent characteristics. Processor 190 may be, for example, a microprocessor, computer or the like. Gamma ray attenuation is typically measured, in the two-energy example, at one high energy emission line, to differentiate between the gas and liquid components, and at a relatively lower energy emission line, to differentiate between the oil and water phases within the liquid component. In this manner, gamma ray attenuation count rates I1 and I2 are used to determine the water, oil and gas volume fractions. The phase fractions are combined with the phase densities at line conditions, pressure P, differential pressure $\Delta p$ and temperature T to determine total effluent density and flow rate. The phase volume fractions then may be used to determine phase flow rates from the total effluent flow rate.

Figure 2:
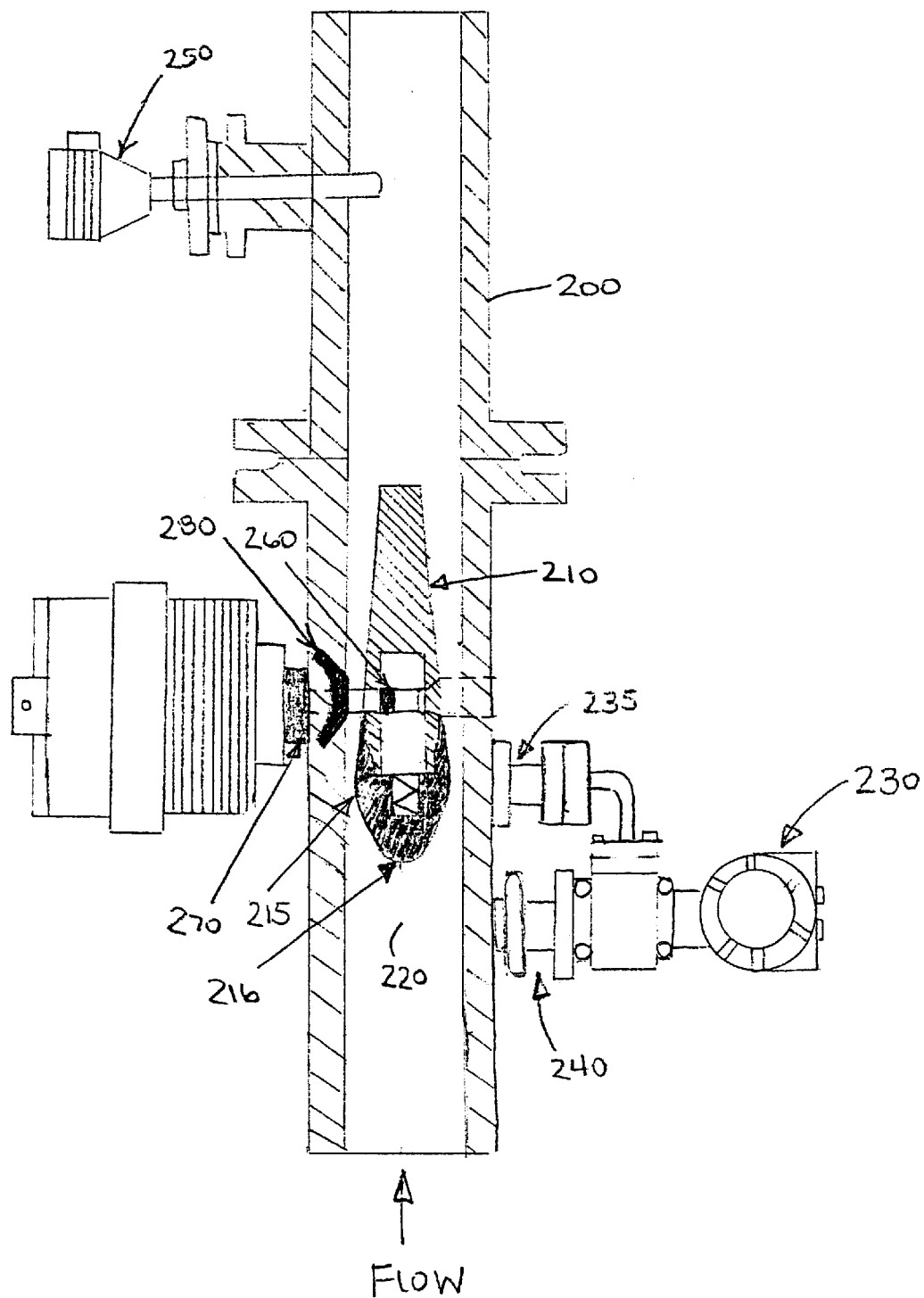
FIG. 2 shows a longitudinal sectional view through the preferred embodiment of a measurement apparatus of the present invention including a specially designed truncated cone shaped CFRE window at the gamma ray detector.

FIG. 2 represents a pictorial layout of one exemplary embodiment of the present invention. The apparatus includes a meter body 200 having a Venturi 210 with the narrowest section at the throat 215. In the preferred embodiment, Venturi 210 is designed to be capable of a large flow range by comprising a removable and exchangeable central Venturi nose cone 216. Using the same meter body 200, the flow rate range can be modified in situ by exchanging the central Venturi nose cone 216 to maintain the proper beta ratio for measurement accuracy. The beta ratio squared ($\beta^2$) is equal to the restricted cross-sectional area of the pipe divided by the full cross-sectional area of the pipe. This exchangeable central Venturi nose cone 216 has the advantage of minimizing lifetime meter costs since flow ranges can be modified without purchasing a new meter, and therefore no additional installation or downtime costs are incurred.

Like the apparatus in FIG. 1, the pipe section 200 is shown disposed vertically with flow up through the Venturi 210 as symbolized by the flow arrow. As the effluent flows through the Venturi 210, the throat 215 induces a pressure drop $\Delta p$ between upstream level 220 and throat 215. The pressure drop is measured by means of a differential pressure transmitter 230 connected to transducers at pressure measurement ports 235 and 240. Port 240 corresponds to upstream level 220 and port 235 corresponds to throat 215. The temperature transmitter 250 is located above and downstream of Venturi 210. A pressure transmitter (not shown) is located at upstream level 220.

A gamma ray source 260 preferably generates gamma ray emission lines at multiple energy levels. In the preferred embodiment, the radioactive source 260 is selected such that at least two suitable energy levels are emitted to allow the phase volume fractions to be determined. One exemplary embodiment of the present invention utilizes an Americium-241 radioactive gamma ray source 260, located in the measurement section, to provide gamma rays of up to five energies ranging from approximately 14 keV to approximately 60 keV. The gamma rays traverse the process flow, where they are either absorbed by the fluid or are acquired by a solid-state detector 270 mounted on the exterior of the pipe. Due to the relatively low energy of the Americium-241 gamma rays compared to the energy levels of other radioisotopes, the intervening liquid path length between source 260 and detector 270 is restrained to approximately 15 to 25 millimeters, and preferably to approximately 20 millimeters.

Solid-state detector 270 measures the gamma ray attenuation count rates representing the number of photons detected per measurement period at each of the energy levels. In the context of the present invention, the term solid-state detector refers to a semiconductor diode detector that is compact and has a high resolution in the energy range of the gamma ray source 260. In the exemplary embodiment, the solid state detector 270 comprises two or more radiation detecting surfaces and a filter preventing certain of the energy levels from passing through to the detecting surface. Such a multiple surface detector and filter is disclosed in European Patent Specification EP 0,696,354 B1. Another embodiment would provide suitable measurement accuracy using a solid state detector 270 having only a single detecting surface and without a filter. Regardless of the solid state detector 270 configuration, the preferred embodiment includes a suitable cooling means that enhances the resolution and efficiency of the semiconductor to distinguish the closely spaced low-energy lines from source 260, such as the Peltier element disclosed in EP 0,696,354 B1.

To avoid the high gamma ray losses that would otherwise occur on passage through the pipe walls, it is preferred that a low radiation absorption section or window 280, be installed to provide process isolation in the vicinity of the measurement path. The window is preferably comprised of Carbon Fiber Reinforced Epoxy (CFRE) with a high percentage of carbon fibers to maintain low radiation absorption, such as the CFRE composition disclosed in EP 0,696,354 B1, but other materials are suitable such as, for example, boron carbide. The preferred configuration of the low absorption window 280 is a specially designed truncated cone shape shown in FIG. 2 that is incorporated into the pipe wall at the measurement point to increase the transmission of radiation to the detector. This truncated cone shape optimizes the strength of window 280, allowing it to withstand high internal pressures, while also lowering absorption of radiation through the window and simplifying manufacture and assembly as compared to the CFRE liner configuration disclosed in EP 0,696,354 B1.

Signals from differential pressure transmitter 230, temperature transmitter 250, pressure transmitter (not shown) and gamma ray detector 270 are fed to the data processor (not shown) where calculations are performed to determine effluent characteristics. These signals can be used to determine the phase volume fractions, total and phase flow rates, total mixture density, and salinity of the produced water.

The use of Americium-241 or another source with relatively low energy emission lines has various advantages over competing technologies that also employ the gamma-ray absorption principle. The high contrast between water, oil and gas mass attenuation coefficients at the lower energies employed here enhances the accuracy of the phase volume fraction determinations. As energy levels exceed 60 keV, the differential between the oil and water attenuation coefficients is greatly reduced. At the higher energies commonly used in other multiphase meters (e.g. the 30 and 360 keV lines of Ba-133 and the 660 keV line of Cs-137) the contrast between oil and water becomes diminishingly small. Far longer gamma ray attenuation count rate measurement times are then necessary to obtain the same statistical accuracy in the phase volume fraction determinations, and any inhomogeneity in the multiphase flow during this extended measurement period will lead to an error in the derived fractions. By measuring at two distinct gamma ray energies, where the mass attenuation coefficients of the three phases are sufficiently different, a set of linearly independent equations is obtained which can be solved for the water, oil and gas phase volume fractions. However, even with low energy gamma ray sources such as Americium-241, a certain measure of error is introduced in the phase volume fraction determination due to the inhomogeneity of the fluid flow. Certain teachings herein correct the gamma ray count rate in inhomogeneous flow back to an effective count rate for homogeneous flow.

Using a multiple low-energy gamma ray source 260 provides another advantage. A third energy emission line and a suitable method such as that disclosed in U.S. Pat. No. 5,854,820, incorporated by reference herein for all purposes, allows for a determination of produced water salinity which can then be used to automatically compensate measurements for salinity variations in the produced water. This in turn reduces the calibration frequency. Solution of the salinity equations requires longer acquisition periods. However, salinity changes in the field generally occur over a relatively longer time period and hence the compensation for salinity is easily achieved within the time cycles for most applications.

Figure 3:
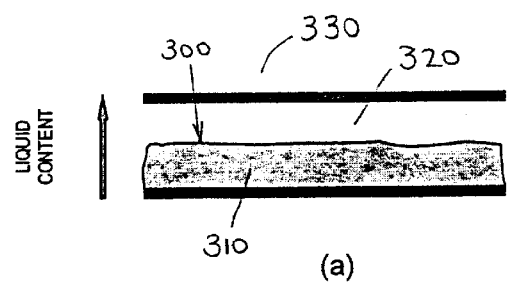
FIG. 3(*a*) shows a simplified illustration of a homogeneous flow profile and FIG. 3(*b*) shows the associated gamma ray attenuation count rate at the detector.

FIG. 3(a) shows a simplified illustration of a homogeneous flow profile 300 in a stratified flow where the liquid content 310 and gas content 320 remains constant along the pipe section 330. FIG. 3(b) shows a simplified measured count rate $I_M(t)$ profile 340 for the gamma ray attenuation at the detector corresponding to the homogenous flow profile 300 for FIG. 3(a). The $I_M(t)$ lies between $I_V$ for the empty-pipe (vacuum) count rate that is roughly equal to the count rate for a 100% gas-filled pipe and $I_L$ count rate for a 100% liquid-filled pipe.

Figure 4:
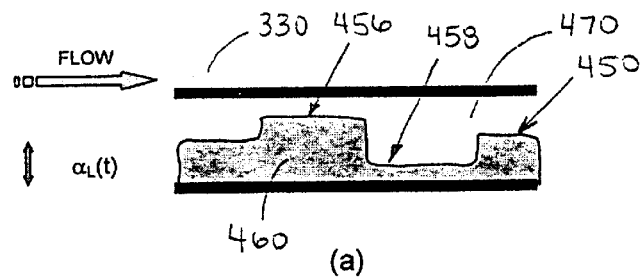
FIGS. 4(*a*) shows a simplified illustration of an inhomogeneous flow profile and FIG. 4(*b*) shows the associated gamma ray attenuation count rates at the detector.

Similarly, FIG. 4(a) shows a simplified illustration of an inhomogeneous flow profile 450 in stratified and fluctuating flow where the liquid content 460 and gas content 470 vary along the pipe section 330. FIG. 4(b) shows a simplified measured count rate $I_M(t)$ profile 480 corresponding to the inhomogeneous flow profile 450. The $I_M(t)$ again lies between $I_V$ for the empty-pipe count rate and $I_L$ count rate for a 100% liquid-filled pipe. It should be noted that, in absolute terms, $I_L$ would differ depending upon the liquid composition (i.e. whether it is oil, water or a mixture of oil and water).

In this example, the volume of liquid and gas passing through pipe section 330 is the same in the homogeneous flow profile 300 and the inhomogeneous flow profile 450. However, due to the exponential nature of the gamma ray absorption process, the net transmitted $I_M(t)$ is different. In essence, the reduced transmission 455 during the short period of high liquid content 456 is not cancelled by the increased transmission 457 during the period of low liquid content 458.

Homogeneous Flow Equations

Figure 5:
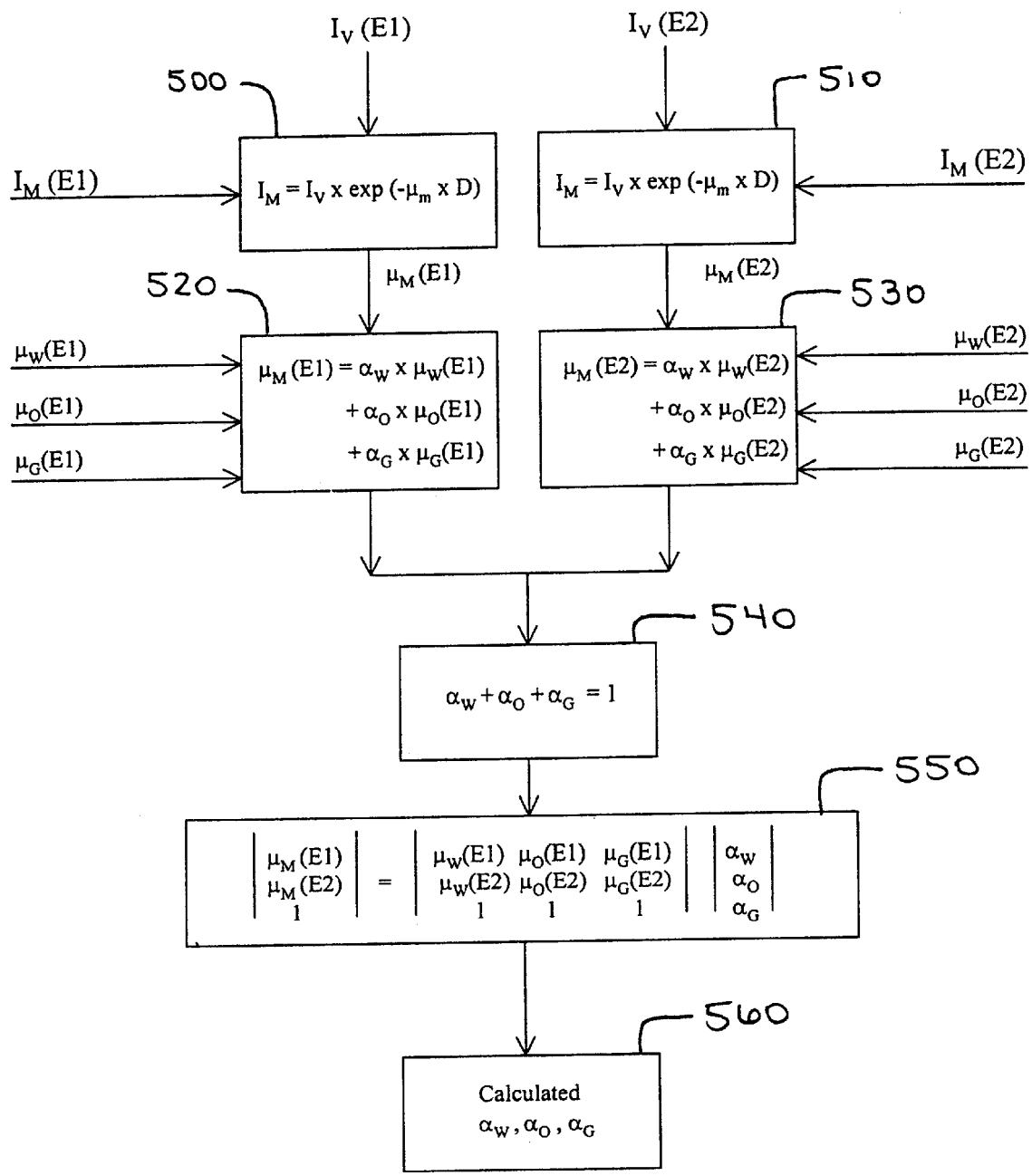
FIG. 5 is a block diagram illustrating a data processing method for determining effluent phase percentages in homogeneous flow profiles.

FIG. 5 is a block diagram describing the process of determining three phase volume fractions, $\alpha_W$ for water, $\alpha_O$ for oil and $\alpha_G$ for gas, in a multiphase fluid using the gamma ray absorption method. The gamma ray count rate $I_M$ measurements must be made at a minimum of two gamma ray energies E1 and E2, although additional energy emission lines may be readily included to improve the accuracy of the result. For example, using Americium-241 with five energy emission lines, gamma ray count rates may be measured at all five levels and a least squares fit method can be applied to improve the accuracy of the phase volume fraction determinations.

FIG. 5 is based on the simplest case of Dual Energy Gamma Ray Absorption at E1 and E2 where for a multiphase fluid, the transmitted (or measured) count-rate $I_M$ at a given energy E1 is equal to the empty-pipe (or vacuum) count-rate $I_V(E1)$ modified by an exponential factor that describes the gamma ray absorption over the fluid pathlength, D. That relationship between $I_M$ and $I_V$ at E1 is expressed at Step 500 as:

$$I_M(E1)=I_V(E1)\cdot\exp\{-\mu_M(E1)\cdot D\} \quad (1)$$

Step 510 shows the same relationship between $I_M$ and $I_V$ at E2.

The magnitude of gamma ray absorption is determined by the gamma ray linear attenuation coefficient of the mixture, $\mu_M(E1)$. The $I_M$ and $I_V$ count rates at E1 and E2 are measured values that are provided as input values to the processor in Steps 500 and 510 to solve for $\mu_M(E1)$ and $\mu_M(E2)$.

Steps 520 and 530 show another expression for the gamma ray mass attenuation coefficients $\mu_M(E1)$ and $\mu_M(E2)$ that are simply equal to the sum of the water, oil and gas coefficients, weighted by their phase fractions as follows:

$$\mu_M(E1)=\alpha_W\cdot\mu_W(E1)+\alpha_O\cdot\mu_O(E1)+\alpha_G\cdot\mu_G(E1) \quad (2)$$

The fluid calibration constants $\mu_W$, $\mu_O$, and $\mu_G$ are provided as input values to the processor in Steps 520 and 530, and they are generally determined by measuring at each energy level E1 and E2 using samples of the pure fluids during meter set-up.

The expressions for $\mu_M(E1)$ and $\mu_M(E2)$ together form a pair of simultaneous equations that can be solved for two of the unknown phase volume fractions, $\alpha_W$, $\alpha_O$, and $\alpha_G$. The third equation in Step 540 is derived from the fact that all three phase volume fractions must add to unity (100%). Including this constraint equation, the problem can be written in Step 550 in a convenient matrix form as follows:

$$\begin{bmatrix} \mu_M(E_1) \\ \mu_M(E_2) \\ 1 \end{bmatrix} = \begin{bmatrix} \mu_W(E_1) & \mu_O(E_1) & \mu_G(E_1) \\ \mu_W(E_2) & \mu_O(E_2) & \mu_G(E_2) \\ 1 & 1 & 1 \end{bmatrix} \cdot \begin{bmatrix} \alpha_W \\ \alpha_O \\ \alpha_G \end{bmatrix} \quad (3)$$

The array on the left contains the measured data (gathered per acquisition cycle) and the array on the right contains the set of phase volume fractions to be determined. The central array holds the fluid calibration constants generally determined based on samples of the pure fluids. Solving for the three equations with the three unknowns yields the calculated values in Step 560 for the three phase fractions, $\alpha_W$ for water, $\alpha_O$ for oil and $\alpha_G$ for gas.

Inhomogeneous Flow

The flow chart of FIG. 5 assumes that the mixture remains homogeneous throughout the measurement period, $\tau$. In practice, this is not always true, particularly at higher gas contents. As seen in FIGS. 3(a), 3(b), 4(a), and 4(b) the same volumes of oil, water and gas passing through the pipe section 330 result in different measured count-rates $I_M$ for homogeneous and inhomogeneous flow. This is due to the physical nature of the gamma ray absorption process, the magnitude of which varies exponentially rather than linearly with the liquid volume fraction $\alpha_L$ (oil+water).

Figure 6:
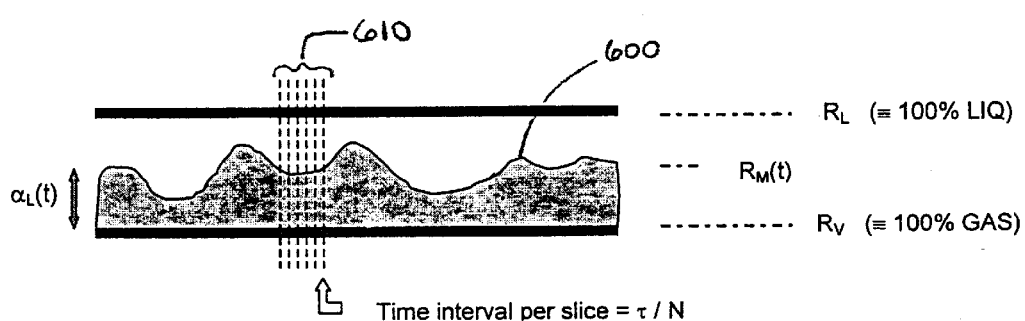
FIG. 6 shows a graph illustrating the proportional relationship between the logarithm of the gamma ray attenuation count rate through a liquid/gas mixture and the liquid volume fraction.

FIG. 6 shows a much more complex flow pattern 600 likely to be encountered in practice that results in count-rate perturbations that may be quite large. This can lead to substantial errors in the phase volume fractions when computed by the method described for homogeneous fluids in FIG. 5. The logarithm of the instantaneous measured count-rate $I_M(t)$ is expressed as quantity $R_M(t)$ and varies in direct proportion to the liquid fraction $\alpha_L(t)$. The quantities $R_V$ and $R_L$ correspond to the logarithms of the count-rates $I_V$ measured with the pipe empty (effectively 100% gas) and $I_L$ measured with the pipe 100% full of liquid, respectively. The preferred embodiment employs a correction method whereby the full measurement period τ, is sub-divided 610 into N time slices j of duration τ/N and the mixture is assumed to be approximately homogeneous over each time slice j. The measurement period τ is tuned to suit a given flow condition, and the more rapidly changing the flow condition, the shorter the time period selected. For inhomogeneous flow, the measurement period τ is preferably 1 to 5 seconds and for very stable homogeneous flow conditions, a measurement period of up to 30 seconds may be selected. The time-slice duration τ/N is determined based on a balance between being sufficiently short to account for fluid condition changes while being long enough to acquire sufficient count rates within the time slice to achieve acceptable statistical accuracy. Depending upon variations in the flow, 10 to 100 millisecond time slices are preferred.

Figure 7:
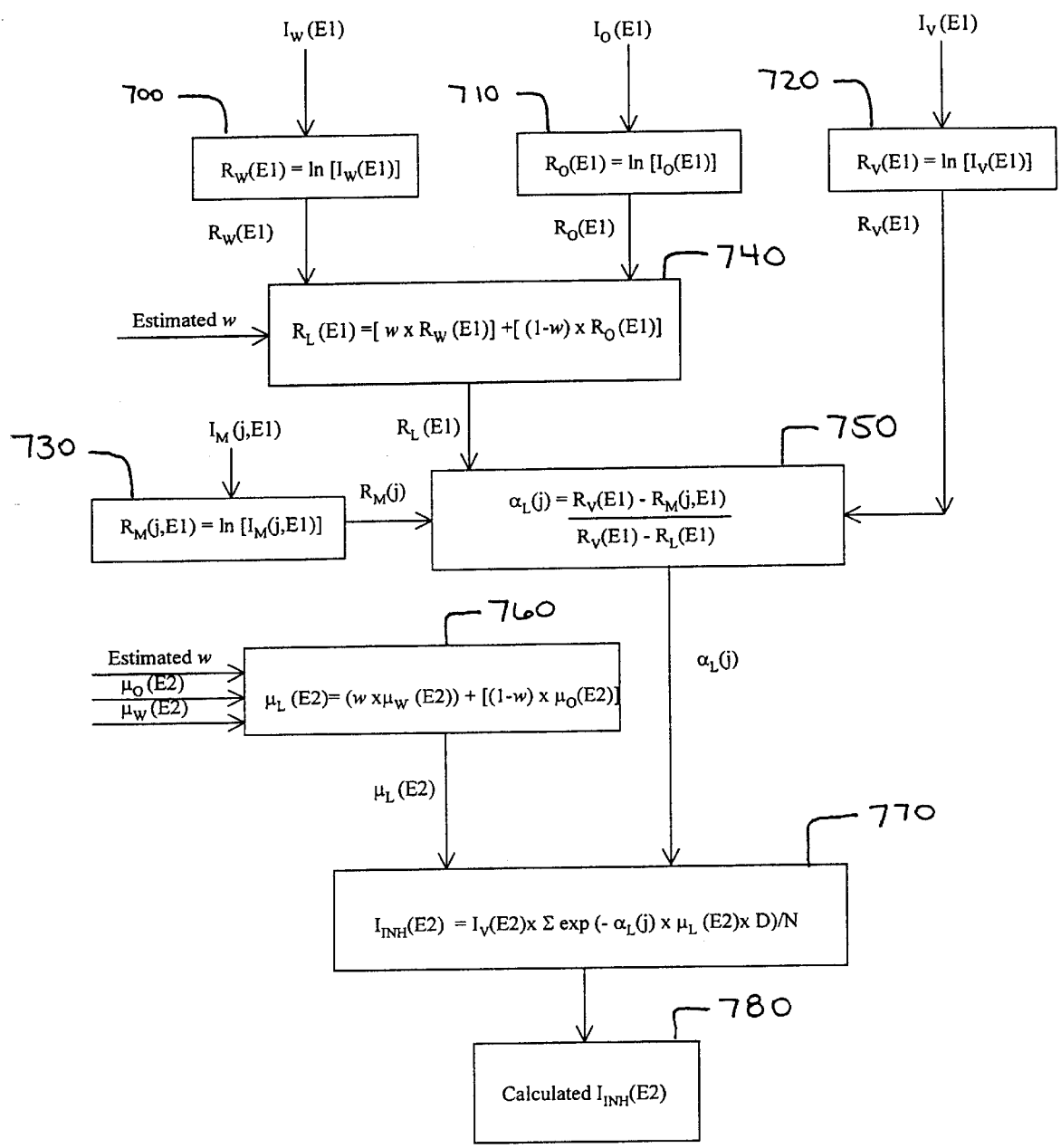
FIG. 7 is a block diagram illustrating the data processing method of the preferred embodiment for determining a liquid volume fraction from the time slice count rates measured by fast sampling over the measurement time period, to then calculate the theoretical inhomogeneous count rates.
Figure 8:
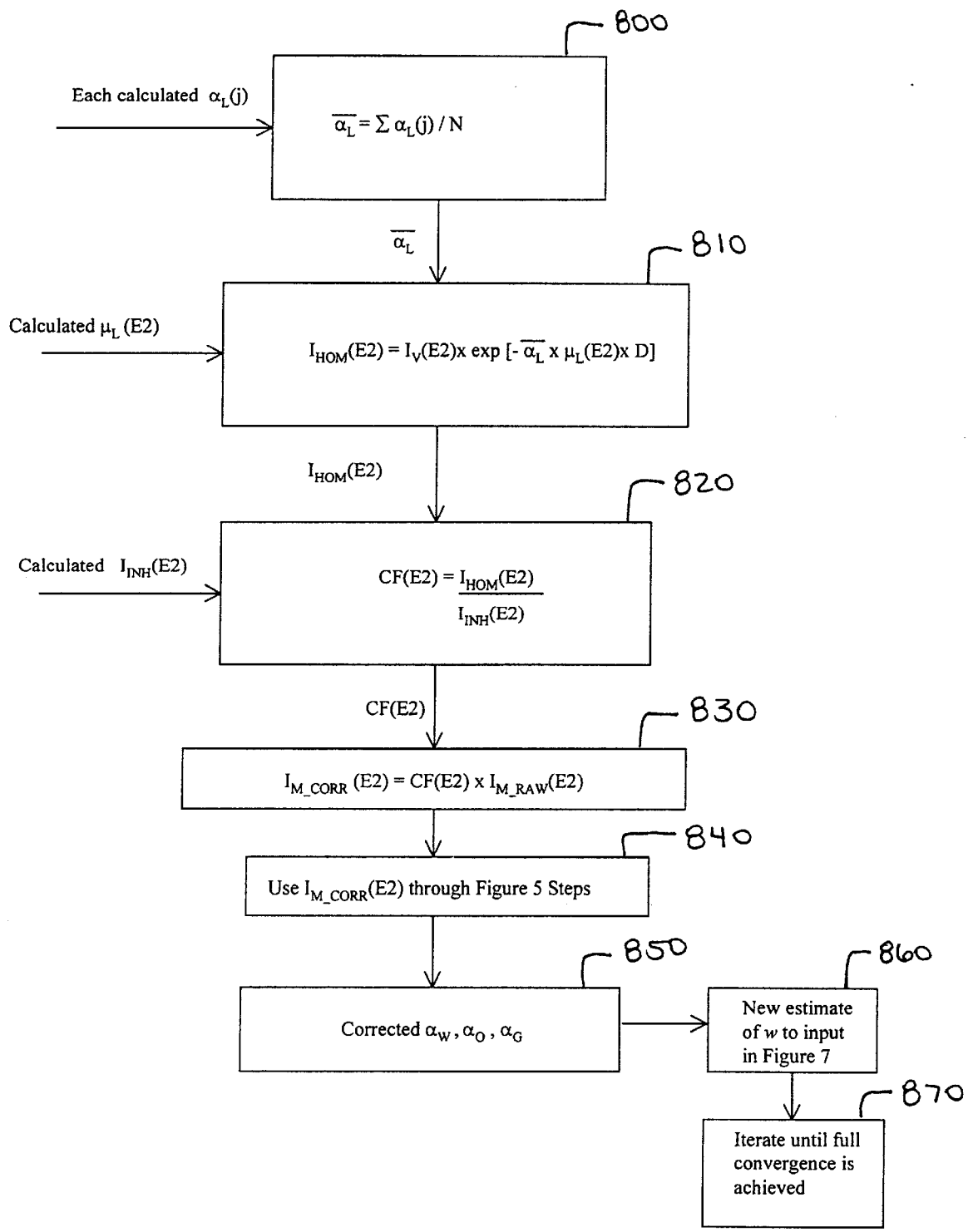
FIG. 8 is a block diagram illustrating the data processing method of the preferred embodiment for correcting a measured inhomogeneous count rate back to an equivalent homogeneous count rate.

FIGS. 7 and 8 illustrate the correction calculation method for inhomogeneous flow phase volume fraction determinations. In particular, FIGS. 7 and 8 illustrate the method as applied to a two energy level example, and specifically as applied to the second energy level E2. As will be appreciated by one of ordinary skill in the art, the teachings herein are not limited to the specifics of FIG. 7 and 8. For example, a greater or fewer number of energy levels could be used or the technique could be refined for additional flow components or phases. Therefore, although FIGS. 7 and 8 apply the method to energy level E2, the method is equally applicable to all other energy levels, including E1 in the two-energy level example.

Referring now to FIG. 7, the count rate at E1 is sampled at a frequency N/τ in order to estimate the liquid fraction distribution at Step 750, whereas the count rate at E2 is measured for the entire measurement period τ. $R_W$, $R_O$, $R_V$ and $R_M$ are defined to be the logarithms of the water (Step 700), oil (Step 710), empty-pipe (Step 720) and mixture (Step 730) count-rates, respectively at energy E1. With $R_W$ and $R_O$ as inputs into Step 740 along with an estimate of the water cut percentage w, the logarithm $R_L$ is determined for the given energy level, E1. $R_L$, $R_V$ and $R_M(t)$ are inputs into Step 750 for a determination of the liquid fraction $\alpha_L$ within each time slice j, which is given by:

$$\alpha_L(j) = \frac{R_V(E1) - R_M(j, E1)}{R_V(E1) - R_L(E1)} \quad (4)$$

This simple relationship is possible because the $\alpha_L(t)$ varies in direct proportion to the logarithm $R_M(t)$ of the transmitted count rate where time t represents a general elapsed time within the measurement period. It is reasonable to presume here that gamma ray absorption in the gas is negligible.

The liquid fraction $\alpha_L(j)$ is determined for each time slice j within the nominal measurement cycle, τ, where j=1, . . . ,N, and then this information is used in the remaining steps shown in FIGS. 7 and 8 as applied to the second energy level E2 to estimate what the measured count-rates would have been, had the same volumes of liquid and gas remained homogeneously mixed during that period τ (as the phase fraction algorithms of FIG. 5 require). As illustrated thus far, Steps 700 to 750 should be calculated at energy level E1 using the fast sampling rate. The remaining steps are described with respect to the second energy level E2, although they are equally applicable to all energy levels, including E1.

Step 760 shows the liquid linear attenuation coefficient $\mu_L$ expressed as a function of the oil and water linear attenuation coefficients and the water-cut w at the second energy level E2:

$$\mu_L(E2) = w \cdot \mu_W(E2) + (1-w) \cdot \mu_O(E2) \quad (5)$$

where w is the same estimate for water cut used at Step 740. Using the number of time slices N, the derived liquid fraction $\alpha_L(j)$, and the present estimate of $\mu_L(E2)$, the theoretical inhomogeneous count rate $I_{INH}(E2)$ can be calculated over the full period τ as shown at Step 770 where $I_{INH}(E2)$ for the second energy level is just:

$$I_{INH}(E2) = I_V(E2) \cdot \Sigma \exp(-\alpha_L(j) \cdot \mu_L(E2) \cdot D)/N \quad (6)$$

Completing this summation yields the $I_{INH}(E2)$ in Step 780. Since $I_{INH}(E2)$ is based on a current best estimate of the water cut w, this theoretical inhomogeneous count rate may differ from the actual total count rate $I_{M-RAW}(E2)$ measured over time period τ.

FIG. 8 continues the correction method by determining an expression for the theoretical homogeneous count rate $I_{HOM}$ for the liquid total volume estimated through the steps in FIG. 7. The steps of FIG. 8 are described with respect to the second energy level E2, although they are equally applicable to all energy levels, including E1.

Starting in Step 800, an equivalent homogeneous liquid fraction is just an average $\overline{\alpha}_L$ determined from each calculated $\alpha_L(j)$ as follows:

$$\overline{\alpha}_L = \Sigma \alpha_L(j)/N \quad (7)$$

Using that average liquid fraction as an input value in Step 810, the theoretical homogeneous rate is calculated as follows:

$$I_{HOM}(E2) = I_V(E2) \cdot \exp\{-\overline{\alpha}_L(j) \cdot \mu_L(E2) \cdot D\} \quad (8)$$

Inputting that expression into Step 820 along with the calculated $I_{INH}(E2)$ from Step 780 on FIG. 7, a correction factor CF for the second energy level E2 can be developed as follows:

$$CF(E2) = \frac{I_{HOM}(E2)}{I_{INH}(E2)} \quad (9)$$

As expressed in Step 830, CF(E2) is multiplied by the total measured count-rate $I_{M-RAW}(E2)$ for the measurement period τ to provide an equivalent homogeneous or corrected count rate $I_{M-CORR}(E2)$. In the same way, the total measured count rates for the first energy level $I_{M-RAW}(E1)$ will be corrected to $I_{M-CORR}(E1)$. The method may also be extended to other gamma ray lines detected by the measurement system. This correction thereby converts the measured count rates $I_{M-RAW}(E1)$ and $I_{M-RAW}(E2)$ to equivalent homogeneous or corrected rates $I_{M-CORR}$. At Step 840, these $I_{M-CORR}$ values for each energy level can be used directly in the algorithms of FIG. 5 to evaluate the full set of corrected phase volume fractions as shown at Step 850. Therefore, in summary, the method converts the measured count rates (under inhomogeneous flow) into equivalent homogeneous count rates so that the homogeneous equations of FIG. 5 are applicable for determining the phase volume fractions.

One assumption used above in determining the liquid fraction $\alpha_L$ as a function of time is that the reference count rate $R_L$ for the liquid phase is known a priori which requires knowledge of the water-cut w. However, w relates to one of the parameters to be measured. A first cycle of the calculation is therefore made using an estimated value for w as shown at Step 740 and Step 760 in FIG. 7. The full phase volume fraction calculation determined using $I_{M\_CORR}$ provides a better estimate of this parameter, and then as shown at Step 860, this w is fed back as a starting value into Step 740 and Step 760 in FIG. 7. Step 870 indicates the requirement that the entire computation be iterated until full convergence is achieved.

The above discussion is meant to be illustrative of the principles of the present invention. Numerous variations and modifications will become apparent to those skilled in the art once the above disclosure is fully appreciated. It is intended that the following claims be interpreted to embrace all such variations and modifications.

What is claimed is:

1. An apparatus for measuring the phase volume fractions of a multiphase mixture, comprising:

a conduit having a reduced diameter section for restricting the flow of the mixture as it passes through said conduit;

a source of radiation for transmitting rays of at least two energy levels through the mixture;

a detector that detects the attenuation count rates of said rays at each energy level;

a section of low radiation absorption material that replaces a wall portion of said conduit in the area of said detector; and a processor coupled to said detector, said processor calculating said phase volume fractions from said count rates at each energy level.

2. The apparatus of claim 1 wherein said reduced diameter section comprises a converging Venturi having a removable nose cone section that can be exchanged in situ.

3. The apparatus of claim 1 wherein said section comprises a truncated cone shaped window.

4. The apparatus of claim 1 wherein said source of radiation comprises an Americium-241 radioactive source.

5. The apparatus of claim 1 wherein said detector includes at least two radiation detection surfaces.

6. The apparatus of claim 1 wherein said detector includes a suitable cooling device.

7. The apparatus of claim 6 wherein said cooling device is a Peltier element or elements.

8. The apparatus of claim 1 wherein said material comprises Carbon Fiber Reinforced Epoxy (CFRE).

9. The apparatus of claim 1 wherein said source produces rays of three or more energy levels.

10. The apparatus of claim 1 wherein said source produces rays of up to five energy levels.

11. The apparatus of claim 1 wherein said detector includes one radiation detection surface.

12. The apparatus of claim 5 further including at least one filter for preventing certain energy levels from passing to at least one of said detection surfaces.

13. A method of measuring the volume fractions of the components of a multiphase mixture under inhomogeneous flow conditions, comprising:

providing a source of radiation that transmits rays of at least two energy levels through the flowing mixture;

measuring, at each energy level, attenuation count rates ($I_M$) for the rays that traversed the mixture, the count rates of at least one energy level being measured over a short time interval compared to a measurement period;

correcting the measured count rates for each energy to equivalent count rates for homogeneous flow conditions; and calculating the volume fractions ($\alpha_W$, $\alpha_G$, $\alpha_O$).

14. A method of measuring the volume fractions of water, oil and gas forming a multiphase mixture flowing under inhomogeneous conditions, comprising:

providing a source of radiation that transmits rays of at least two energy levels along a distance (D) through the flowing mixture;

measuring, at each energy level, attenuation count rates ($I_M$) for the rays that traversed the mixture, the count rates of at least one energy level being rapidly sampled over a measurement period;

calculating, at each energy level, a theoretical inhomogenious count rate;

calculating, at each energy level, a theoretical homogenious count rate;

calculating for each energy level a correction to correct the measured count rates for each energy level to equivalent count rates for homogeneous flow conditions; and calculating the volume fractions ($\alpha_W$, $\alpha_G$, $\alpha_O$) based on the corrected count rates.

15. The method of claim 14 further comprising:

estimating the proportion of water (w) in a liquid volume fraction ($\alpha_L$);

calculating, for said rapidly sampled energy level, the logarithm of a liquid count rate ($R_L$);

calculating, for said rapidly sampled energy level, a liquid volume fraction ($\alpha_L$) per time interval; and calculating, for said rapidly sampled energy level, an average liquid volume fraction over the measurement period.

16. The method of claim 15 further comprising:

iterating through the calculations until no further improvement is gained in the derived phase fractions.

17. The method of claim 15 wherein calculating the logarithm of a liquid count rate ($R_L$) comprises solving the following equation:

$$R_L = [(W \times R_W)] + [(1w) \times R_O], \text{ where:}$$

w=the estimated proportion of water in the liquid volume fraction;

$R_W$=the logarithm of a measured attenuation count rate for a water flow stream obtained by transmitting rays along said distance (D) through the water flow stream; and $R_O$=the logarithm of a measured attenuation count rate for an oil flow stream obtained by transmitting rays along said distance (D) through the oil flow stream.

18. The method of claim 15 wherein calculating a liquid volume fraction ($\alpha_L$) per time interval comprises solving the following equation, for said rapidly sampled energy level:

$$\alpha_L(j) = \frac{R_V - R_M(j)}{R_V - R_L},$$

j=one time interval;

$R_V$=the logarithm of a measured attenuation count rate for a gas flow stream obtained by transmitting rays along said distance (D) through the gas flow stream; and $R_M(j)$=the logarithm of the measured attenuation count rate ($I_M$) through the mixture at time interval j.

19. The method of claim 15 wherein the average liquid volume fraction ($\overline{\alpha_L}$) over the measurement period is calculated by summing the liquid volume fractions calculated for each time interval and dividing that sum by the total number of time intervals.

20. The method of claim 19 wherein calculating at each energy the theoretical homogeneous count rate ($I_{HOM}$) over the measurement period comprises solving the following equation:

$$I_{HOM} = I_V \times \exp\{-\overline{\alpha_L} \times \mu_L \times D\}, \text{ where:}$$

$I_V$ = a measured attenuation count rate for a gas flow stream obtained by transmitting rays along said distance (D) through the gas flow stream; and $\mu_L(E2) = w \times \mu_W(E2) + (1-w) \times \mu_O(2)$ wherein $\mu_W$ and $\mu_O$ are fluid calibration constants.

21. The method of claim 14 wherein the correction factor (CF) is calculated at each energy level by dividing the theoretical homogeneous count rate ($I_{HOM}$) by the theoretical inhomogeneous count rate ($I_{INH}$) over the measurement period.

22. The method of claim 14 wherein the corrected count rates ($I_{M\_CORR}$) are obtained by multiplying the correction factor (CF) by the measured count rates ($I_{M\_RAW}$).

23. The method of claim 13 wherein correcting the measured count rates comprises multiplying the total count rate ($I_{M\_RAW}$) by a correction factor.

24. The method of claim 13 wherein the volume fractions ($\alpha_W$, $\alpha_G$, $\alpha_O$) are calculated using the corrected count rates ($I_{M\_CORR}$) for each energy level.

* * * * *